(12) United States Patent
Negishi

(10) Patent No.: US 6,346,082 B1
(45) Date of Patent: Feb. 12, 2002

(54) DEVICE FOR REGULATING FLUID FLOW RATE, EVACUATION DEVICE FOR A SPHYGMOMANOMETER AND SPHYGMOMANOMETER

(75) Inventor: Sigeto Negishi, Shibukawa (JP)

(73) Assignee: Nihon Seimitsu Sokki Co., Ltd., Shibukawa (JP)

( * ) Notice: Subject to any disclaimer, the term of this patent is extended or adjusted under 35 U.S.C. 154(b) by 0 days.

(21) Appl. No.: 09/341,869
(22) PCT Filed: Feb. 6, 1998
(86) PCT No.: PCT/JP98/00500
§ 371 Date: Jul. 28, 1999
§ 102(e) Date: Jul. 28, 1999
(87) PCT Pub. No.: WO98/34538
PCT Pub. Date: Aug. 13, 1998

(30) Foreign Application Priority Data

Feb. 7, 1997 (JP) ............................................. 9-025448

(51) Int. Cl.$^7$ ................................................. A61B 5/02
(52) U.S. Cl. ........................................ 600/490; 600/498
(58) Field of Search ................................. 600/490–500; 604/249, 256, 905; 251/149, 149.1, 212

(56) References Cited

U.S. PATENT DOCUMENTS 4,497,468 A * 2/1985 Hubbard et al. ............ 605/249
5,806,551 A * 9/1998 Meloul et al. ............ 604/256 X

FOREIGN PATENT DOCUMENTS

| JP | A-6-47008 | 2/1994 |
| JP | A-6-47011 | 2/1994 |

* cited by examiner

*Primary Examiner*—Eric F. Winakur
*Assistant Examiner*—Ryan Carter
(74) *Attorney, Agent, or Firm*—Oliff & Berridge, PLC

(57) ABSTRACT

There are provided a casing (21), a valve element (23) that effects opening/closure of an evacuation port (22), and means for driving (24) that effect opening/closure drive of this valve element. Fine irregularities (23b) are formed on valve element (23). The means for driving comprise: a cylindrical yoke (25); a core (26) provided with a cylindrical part (26a) arranged within the yoke and a flange (26b) that is abutted by one end of the yoke; a magnet (27) arranged within the yoke and that forms magnetic flux in the radial direction; a movable element (28) arranged through the cylindrical part of the core with the valve element mounted at one end; a coil (29) arranged in the gap between the magnet and yoke and fixed at one end of the movable element; and holding members (30) that hold both ends of the movable element and that hold the movable element and coil in non-contacting condition with respect to the core and yoke.

8 Claims, 9 Drawing Sheets

DEVICE FOR REGULATING FLUID FLOW RATE, EVACUATION DEVICE FOR A SPHYGMOMANOMETER AND SPHYGMOMANOMETER

TECHNICAL FIELD

The present invention relates to a fluid flow rate regulation device capable of fine flow rate regulation and an evacuation device for a sphygmomanometer whereby the air that is supplied to an armband can be evacuated with fixed speed, and to a sphygmomanometer of small power consumption, that is capable of miniaturization, and that is capable of measuring with high precision.

BACKGROUND ART

As shown in FIG. 8, a constructional example of a sphygmomanometer comprises: an armband 1 mounted so as to be wound on to an arm or neck or a finger etc. of a human body; a pump 2 that supplies compressed air to this armband 1; a pressure meter 3 that detects air pressure within this armband 1; an electrically-operated evacuation device 4 that evacuates the air within armband 1; and a microcomputer 5 that supplies air of fixed pressure into armband 1 by controlling operation of pump 2 in accordance with a detection signal from pressure meter 3 and that evacuates air with fixed speed from armband 1 by controlling the operation of electrically-operated evacuation device 4.

Conventionally, as shown in FIG. 9 and FIG. 10, electrically-operated evacuation device 4 comprises: a bobbin 6 having a through-hole 6a and with a coil 6b wound at its periphery; a practically U-shaped yoke 7 arranged so as to cover one end and the sides of this bobbin 6; a cover 8 that abuts the other end of bobbin 6 and is fixed in the open end of yoke 7, co-operating with this yoke 7 to form a magnetic path from the center of bobbin 6 to one end face and from the sides of bobbin 6 to the other end face; a movable element 9 comprising a magnetic element freely slidably mounted within a through-hole 6a of bobbin 6; a main valve body 10 mounted passing through this yoke 7 in a portion of yoke 7 covering one end of bobbin 6 and that is inserted from one end thereof into the through-hole 6a of bobbin 6 and is arranged facing movable element 9; a valve element 11 made of resilient material that effects opening/closing of an evacuation port 10a by contacting or being separated from this evacuation port 10a formed in main valve body 10, by sliding action of movable element 9, being mounted at the end of movable element 9 facing main valve body 10; and a resilient member 12 interposed between movable element 9 and main valve body 10 that biases movable element 9 in the direction away from main valve body 10.

The conventional electrically-operated evacuation device for a sphygmomanometer constructed in this way is arranged such that, by supplying drive current to coil 6b, movable element 9 is slid against the resilient force of resilient member 12 by the magnetic force which is then generated, causing valve element 11 that is mounted on this movable element 9 to be pressed against main valve body 10, thereby blocking its evacuation port 10a and such that the pressure within this armband 1 is raised to a fixed pressure by supplying a prescribed quantity of air to armband 1 by driving pump 2, after which pump 2 is stopped and [the supply of current] to coil 6b of electrically-operated evacuation device 4 is stopped, thereby causing movable element 9 to be slid in the direction away from main valve body 10 by the resilient force of resilient member 12, opening evacuation port 10a and allowing air to be evacuated from armband 1.

Also, it is arranged to keep the rate of evacuation constant by controlling the mode of current passage or stoppage thereof to coil 6b.

However, in a conventional electrically-operated evacuation device for a sphygmomanometer constructed in this way, movable element 9 can move freely in the radial direction of bobbin 6; as a result this movable element 9 comes into contact with the inside wall of bobbin 6, generating a frictional force on sliding of movable element 9. There is therefore considerable hysteresis in the opening/closing drive of valve element 11 by microcomputer 5, resulting in poor accuracy of pressure reduction control of armband 1 and so imposing limitations on the precision of the sphygmomanometry.

Since this frictional resistance changes depending on the attitude of the electrically-operated evacuation device for a sphygmomanometer, there is also the inconvenience that the precision of the sphygmomanometry varies depending on the attitude in which the sphygmomanometer is arranged.

Also, in order to cause movable element 9 to slide in the direction such as to block evacuation portion 10a, it was necessary to generate in coil 6b sufficient attractive force to overcome the resilient force of resilient member 12 and the frictional resistance, so the drive current supplied to coil 6b became large, causing an increase in power consumption.

Also, movable element 9 being formed by a magnetic body, its weight is considerable and this also tends to increase the drive current.

Furthermore, although, in order to miniaturize the electrically-operated evacuation device for a sphygmomanometer it is necessary to make the number of turns of coil 6b small and the external diameter of bobbin 6 small, if the number of turns of coil 6b is made small, its attractive force becomes small, with the result that the large attractive force which is necessary to move movable element 9 as described above cannot be obtained.

Also, although it might be thought that miniaturization of the electrically-operated evacuation device for a sphygmomanometer could be achieved while maintaining the number of turns of coil 6b by reducing the weight of movable element 9 by making it smaller and employing an external diameter of small dimensions, making movable element 9 small reduces the attractive force on movable element 9 for the same magnetic flux density; this therefore tends to result in incomplete operation of the movable element 9 and so is not an effective remedy.

With the foregoing in view, it is an object of the present invention to provide a fluid flow rate regulation device capable of fine flow rate regulation and an evacuation device for a sphygmomanometer whereby the air that is supplied into an armband can be evacuated with a constant speed, and a sphygmomanometer whose power consumption is small, which can be made of small size, and which is capable of measurement with high accuracy.

DISCLOSURE OF THE INVENTION

A fluid flow rate regulation device according to a first invention for solving the above problem is provided comprising a fluid passage port and a valve element that effects opening/closure of this fluid passage port, in which the flow rate of fluid flowing through said fluid passage port is regulated by regulating the degree of opening/closure of this valve element wherein: fine irregularities are formed in said fluid passage port and/or valve element in at least a portion where the fluid passage port and valve element make contact.

Also, a second invention constituting an aspect of this first invention is provided wherein the portion in said fluid passage port and/or valve element where at least the fluid passage port and valve element make contact is constituted by a resilient member.

Also an evacuation device for a sphygmomanometer according to a third invention is provided whereby air that is fed into an armband comprised by the sphygmomanometer is gradually evacuated, comprising:

an evacuation port whereby the air that is fed into said armband is evacuated and a valve element that performs opening/closure of this evacuation port, wherein:

fine irregularities are formed on a portion in said evacuation port and/or valve element where at least the evacuation port and valve element make contact.

According to a fourth invention constituting an aspect of this third invention there is provided an evacuation device for a sphygmomanometer according to claim 3 wherein the portion in said evacuation port and/or valve element where at least the evacuation port and valve element make contact is constituted by a resilient member.

Also, an evacuation device for a sphygmomanometer according to a fifth invention is provided whereby air that is fed into an armband comprised by the sphygmomanometer is gradually evacuated, comprising:

a casing; a valve element that performs opening/closure of an aperture arranged in this casing; a cylindrical yoke provided with means for driving that drive opening/closure of this valve element, these means for driving being mounted within said casing; a core provided with a cylindrical part arranged concentrically within this yoke and a flange abutted by one end of said yoke; a magnet that forms magnetic flux in the radial direction and that is arranged within said yoke with a separation with respect to said core; a movable element provided through the cylindrical part of said core, with said valve element integrally mounted at one end thereof; coil arranged in the gap between said magnet and the yoke and fixed at one end of said movable element; and holding members interposed between both ends of said movable member and said casing and that holds said movable element and coil in non-contacting condition with respect to said core and yoke.

Furthermore, a sphygmomanometer according to a sixth invention is provided comprising:

an armband; a pump that supplies compressed air to this armband; a pressure meter that detects the air pressure within said armband; an evacuation device that evacuates the air within said armband 1; and a microcomputer that supplies air at constant pressure to said armband 1 by controlling the action of said pump in accordance with the detection signal from said pressure meter, and that evacuates air at a constant velocity from said armband by controlling the action of said evacuation device, wherein:

an evacuation device for a sphygmomanometer according to claim 3 to 5 is employed as said evacuation device.

BEST MODE FOR CARRYING OUT THE INVENTION

An embodiment of the present invention is described below with reference to FIG. 1 to FIG. 7.

Figure 8:
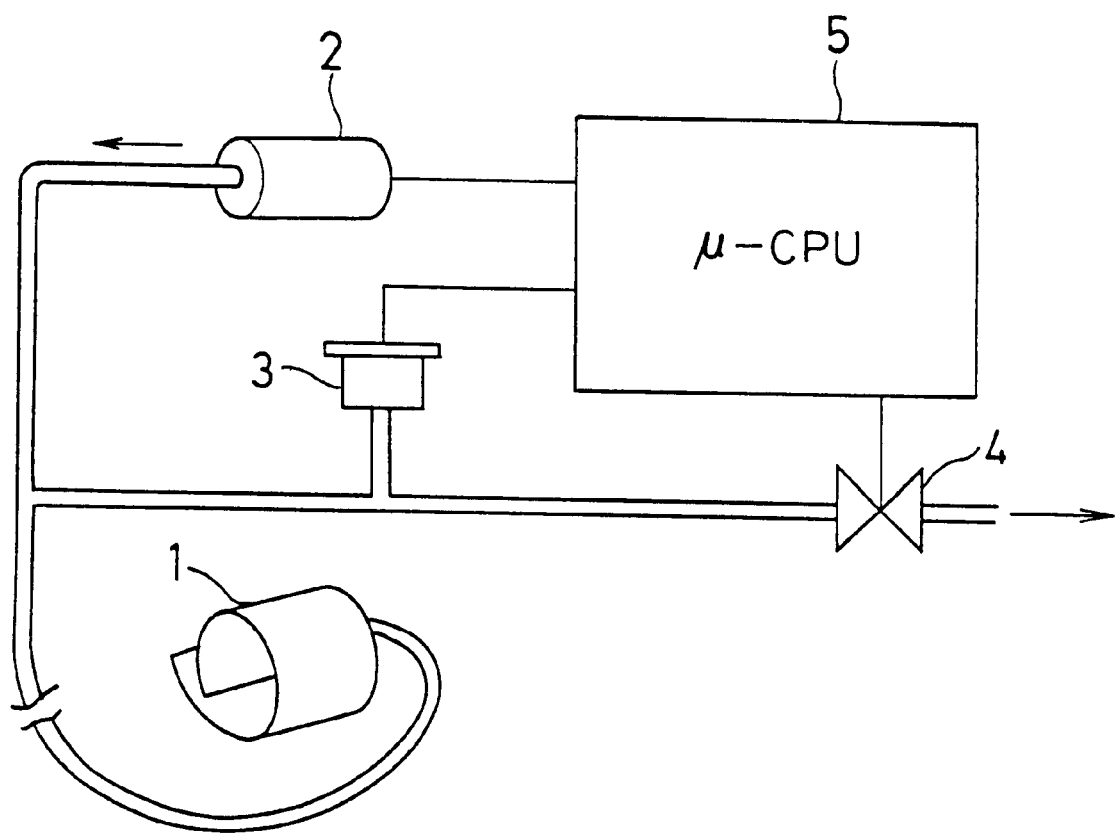
FIG. 8 is a diagram showing an example of the construction of a sphygmomanometer.
Figure 9:
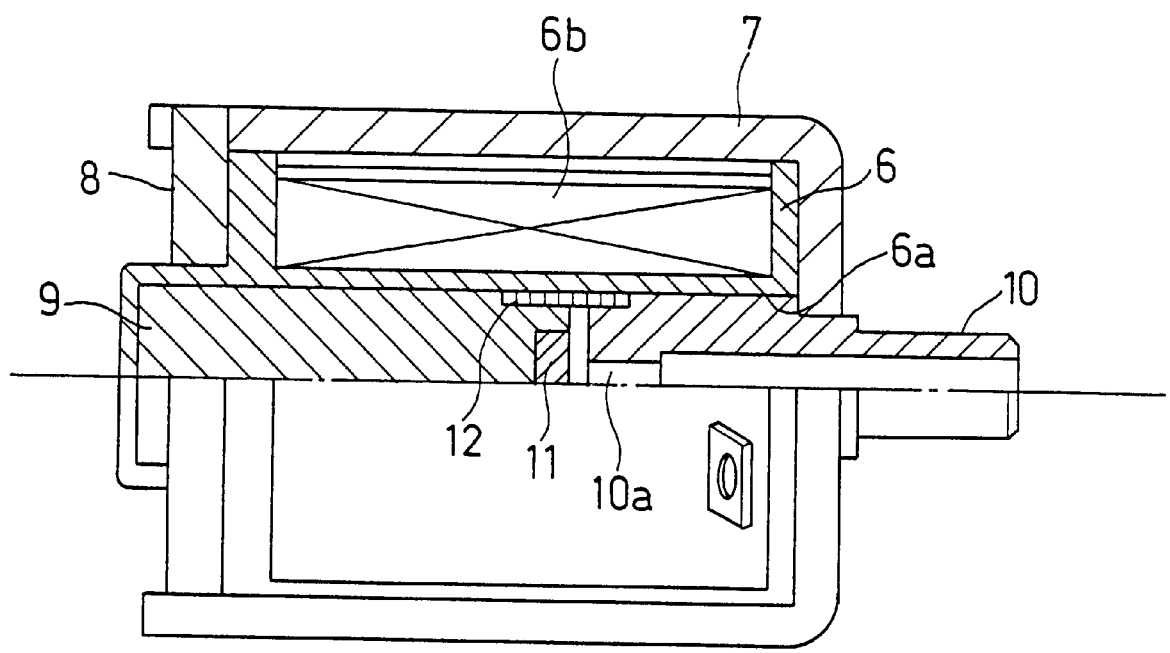
FIG. 9 is a side view with part broken away showing an example of a prior art electrically-operated evacuation device.
Figure 10:
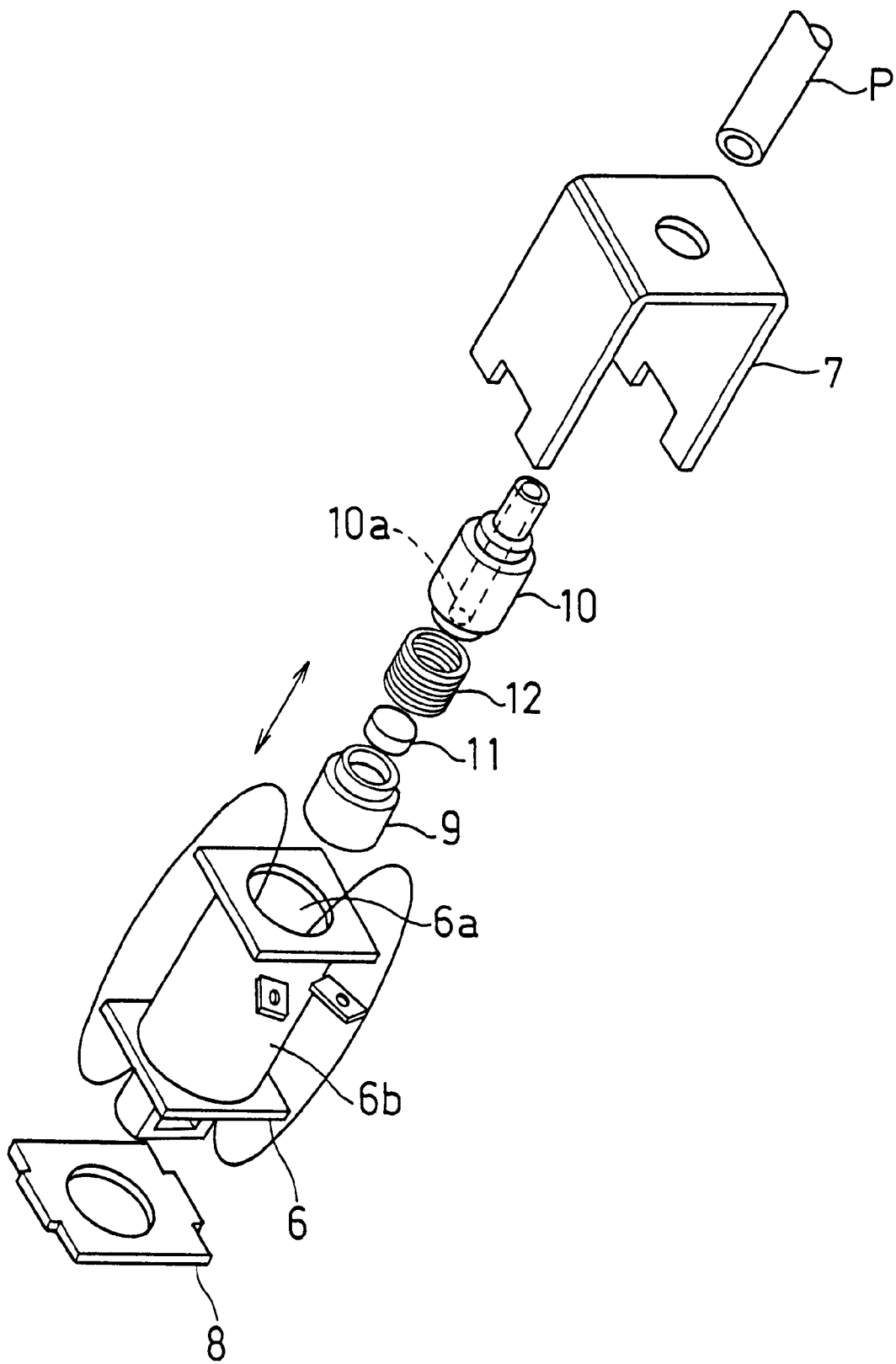
FIG. 10 is an exploded perspective view showing an example of a prior art electrically-operated evacuation device.

In the following description parts which are common with FIG. 8 are given the same reference symbols and further description is omitted.

Figure 1:
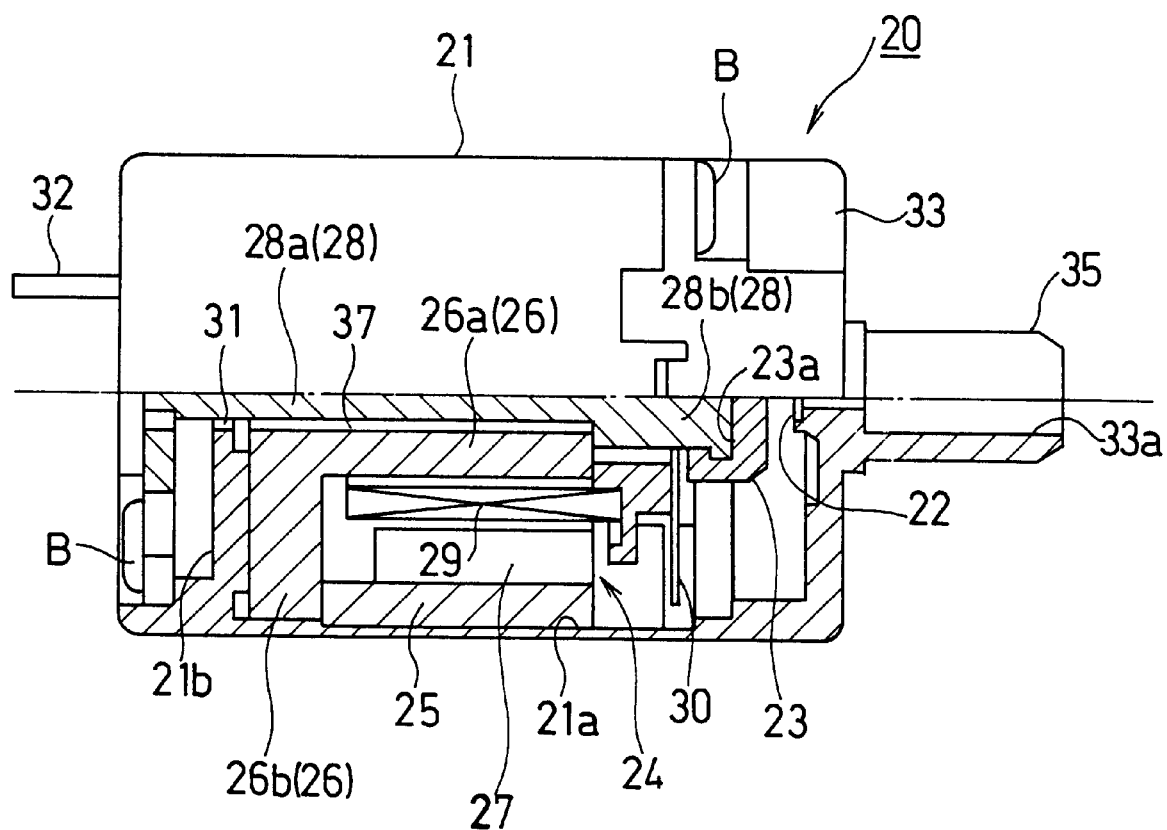
FIG. 1 is a side view with part broken away showing an embodiment of the present invention.

In FIG. 1, reference symbol 20 indicates an electrically-operated evacuation device for a sphygmomanometer according to the present embodiment (hereinbelow called an electrically-operated evacuation device). This electrically-operated evacuation device 20 comprises a casing 21, a valve element 23 that effects opening/closure of an evacuation port 22 provided in this casing 21, and means for driving 24 that drives opening/closure of this valve element 23. In outline, this means for driving 24 comprises: a cylindrical yoke 25 mounted within casing 22, a core 26 equipped with a cylindrical part 26a arranged in co-axial condition within this yoke 25 and a flange 26b that is abutted by one end of yoke 25, a magnet 27 arranged within yoke 25 with a gap with respect to core 26 and that forms magnetic flux in the radial direction, a movable element 28 arranged passing through cylindrical part 26a of core 26 and with valve element 23 integrally mounted at one end thereof, a coil 29 arranged in the gap between magnet 27 and yoke 25 and fixed at one end of movable element 28, and holding members 30 interposed between the two ends of movable element 28 and casing 21 and that hold movable element 28 and coil 29 in non-contacting condition with respect to core 26 and yoke 25.

Figure 2:
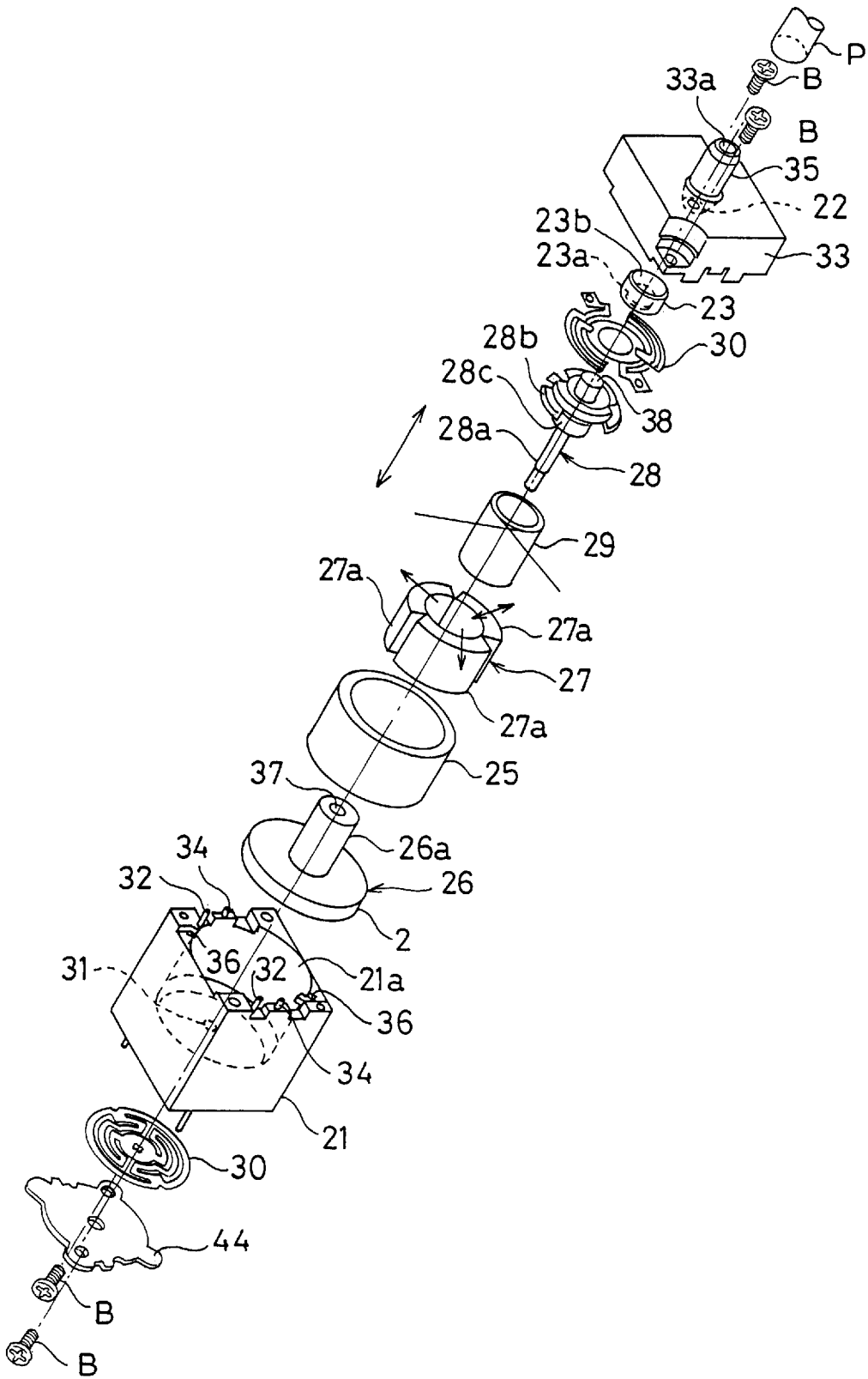
FIG. 2 is an exploded perspective view showing an embodiment of the present invention.

Next, the details of these will be described. As shown in FIG. 2, casing 21 is formed in cubic shape and in its center is formed with an accommodating hole 21a one end of which is blocked, a through-hole 31 being formed in the middle of the bottom thereof, and a pair of terminals 32 that are fixed by solder etc. being arranged passing through in the length direction, the pair of terminals of coil 29 being respectively wound thereon, on the side wall.

Also, a cover 33 is mounted at the end face where the aperture of accommodating hole 21a of casing 21 is formed, being constituted such as to block this aperture. This cover 33 is fixed to casing 21 by a pair of screws B and a pair of projections 34 are provided where a holding member 30 is attached.

Figure 3:
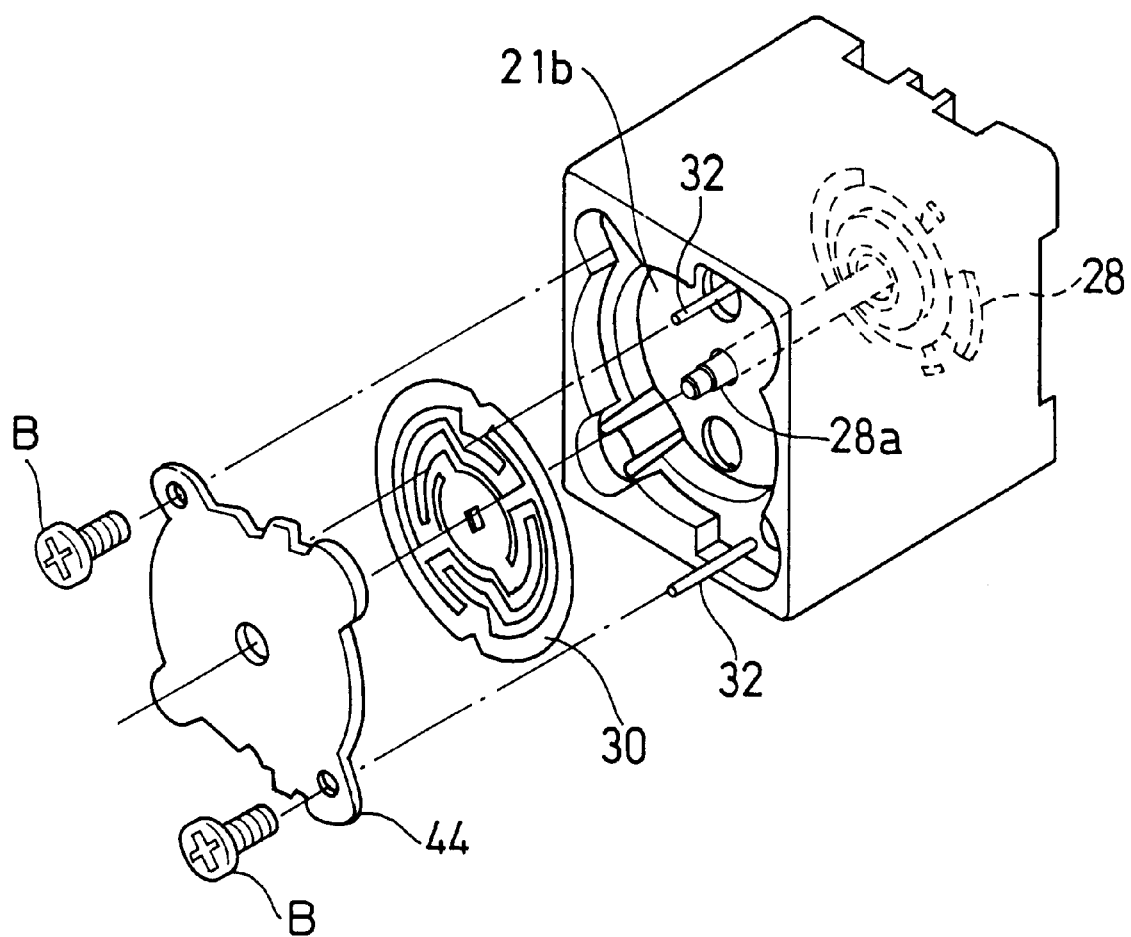
FIG. 3 is a view showing an embodiment of the present invention, being an exploded perspective view showing the bottom face of the casing.

Furthermore, a recess 21b in which is accommodated one of holding members 30 is formed, as shown in FIG. 3, at the end face of casing 21 on the opposite side to the side where the aperture is formed.

In this embodiment, as shown in FIG. 1, evacuation port 22 is formed at the end on the inside of an evacuation passage 33a provided passing through the center of cover 33; this evacuation passage 33a extends for a prescribed length from the end face of cover 33 by means of a cylindrical projection 35 to which an air outlet pipe P is connected, making communication with armband 1 and projecting at the end face on the surface side of cover 33.

Figure 4:
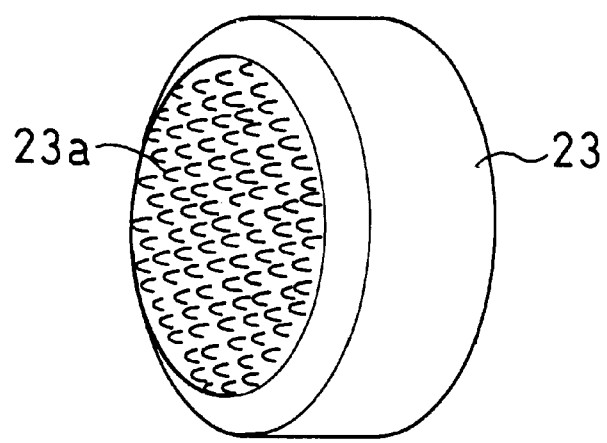
FIG. 4 is an external perspective view of a valve element illustrating an embodiment of the present invention.
Figure 5:
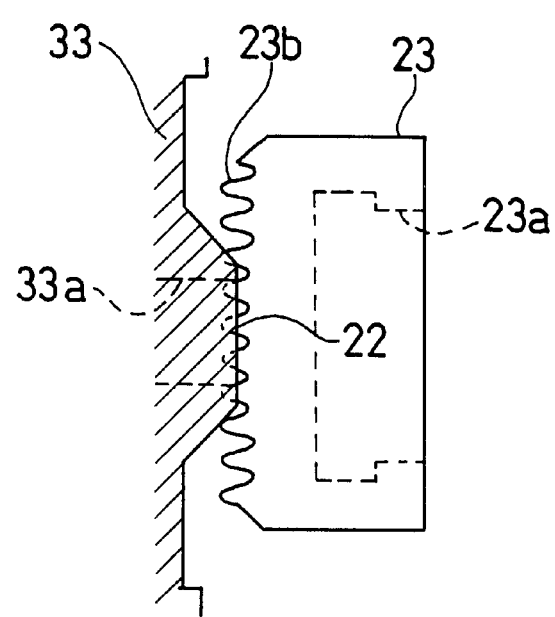
FIG. 5 is a side view to a larger scale showing an embodiment of the present invention, illustrating the condition in which the valve element and evacuation port are in contact.

Valve element 23 is formed In cylindrical shape by resilient material such as rubber, and, as shown in FIG. 4 and FIG. 5, is formed, at one end face thereof, with a recess 23a into which fits one end of movable element 28, and, on the end face opposite evacuation port 22 is formed with fine irregularities 23b.

The size of the individual irregularities of these irregularities 23b is suitably selected depending on the size of the capacity of the air bag incorporated in armband 1 and of evacuation port 10a. In the case of an ordinary sphygmomanometer, the rate of pressure reduction of the air bag is set at 2 to 3 mmHg/sec, so this is set to a size at which this rate of pressure reduction can be accurately maintained.

Yoke 25 is formed in cylindrical shape of magnetic material, its external diameter being formed practically the same as or somewhat smaller that the internal diameter of accommodating hole 21a of casing 21; when it is inserted in accommodating hole 21a, removal from this casing 21 is prevented by engagement of engaging claws 36 provided on the end face of casing 21.

Flange 26b with which core 26 is constituted is formed of practically the same or somewhat smaller external diameter as the internal diameter of accommodating hole 21a of casing 21, cylindrical part 26a being integrally formed at the center thereof.

Through-hole 37 that is formed at the center of this cylindrical part 26a is formed along the entire length of this cylindrical part 26a and is also formed through flange 26b.

This core 26 is positioned coaxially within this accommodating hole 21a by insertion into accommodating hole 21a from the side of flange 26b, and through-hole 37 is coaxial with through-hole 31 formed in the bottom of casing 21.

In this embodiment, magnet 27 is constituted by a plurality of magnet-constituting elements 27a and is overall of cylindrical shape; these magnet-constituting elements 27a are of N polarity on the inside and S polarity on the outside and are integrally mounted in cylindrical fashion on the inside surface of yoke 25 by means of adhesive or the like. Magnetic flux along the radial direction of yoke 25 is formed by these magnet-constituting elements 27a. It should be noted that, although in this example magnet-constituting element 27 was constituted by a plurality (three) of magnet-constituting elements 27a, it could be constituted by a single magnet of cylindrical shape. Also, although in the above embodiment yoke 25 and core 26 were respectively constituted as separate members, they could be integrally constructed by processing such as drawing processing of iron material or permalloy or other magnetic material.

Movable element 28 comprises a shaft 28a formed of lightweight material such as plastics, having an external diameter smaller than the internal diameter of through-hole 37 of core 26 and positioned passing through through-hole 37, projecting into recess 21b through through-hole 31 of casing 21, and a flange 28b formed integrally with one end of this shaft 28a.

A cylindrical pillar 38 is formed at the center of flange 28b on the opposite side to the side where shaft 28a is provided; this cylindrical pillar 38 is mounted on movable element 28 with this valve element 23 surrounding cylindrical pillar 38, by fitting cylindrical pillar 38 into recess 23a of valve element 23.

Figure 6:
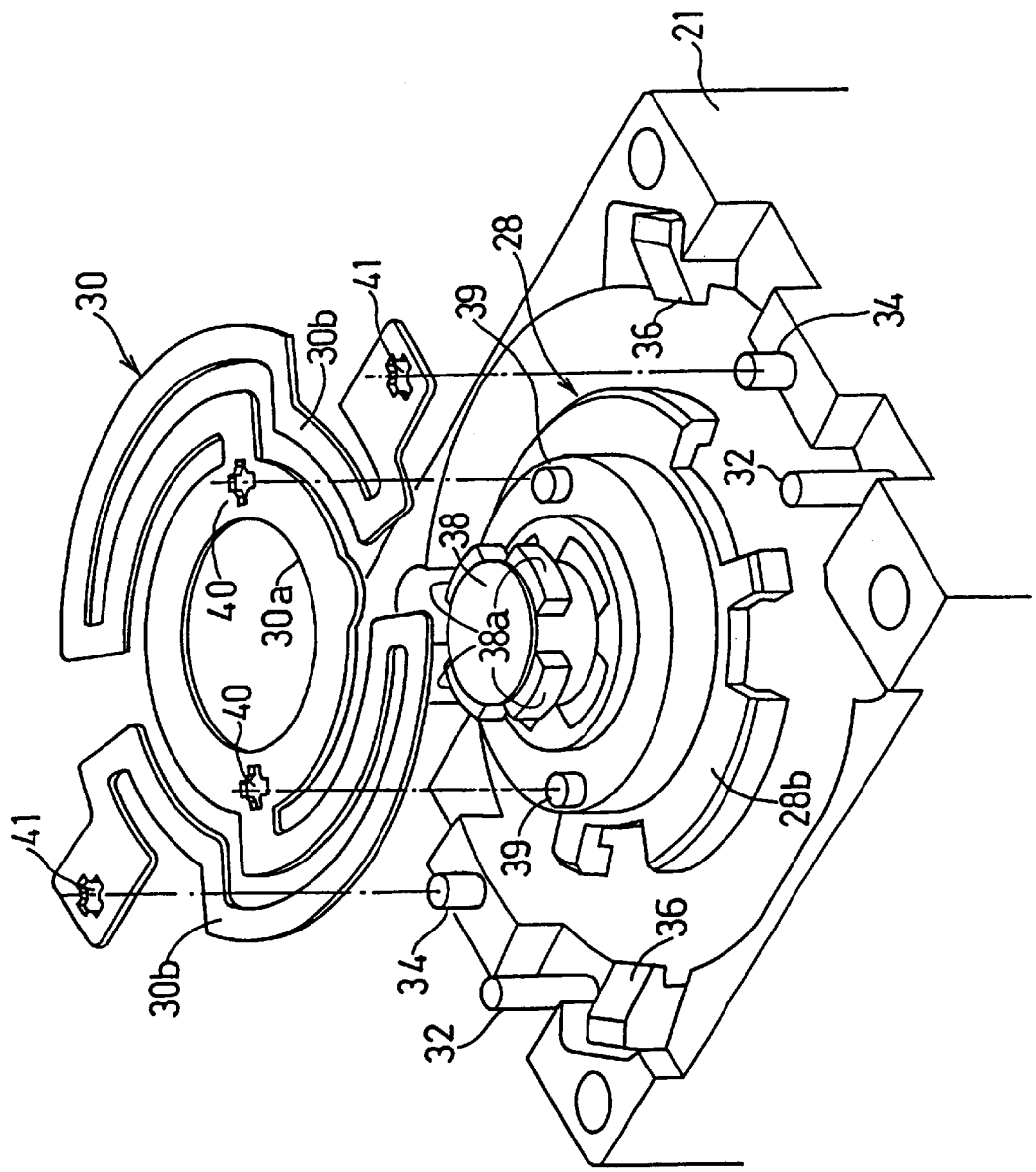
FIG. 6 is an exploded perspective view showing an embodiment of the present invention, illustrating the relationship between the casing and one holding member.
Figure 7:
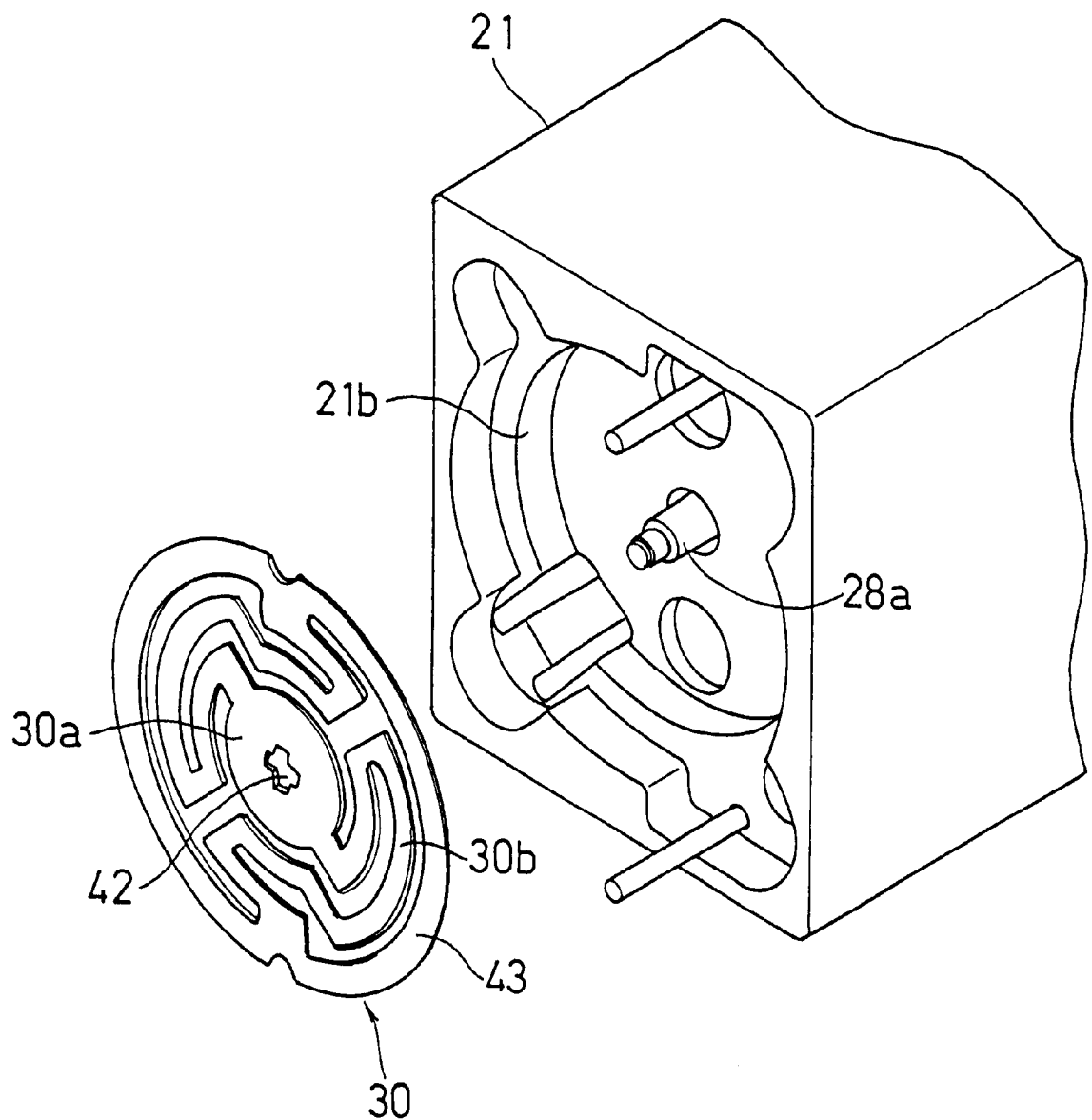
FIG. 7 is an exploded perspective view showing an embodiment of the present invention, illustrating the relationship between the casing and the other holding member.

In addition, a plurality of engagement elements 38a arranged with a separation in the circumferential direction as shown in FIG. 6 are provided on the side face of cylindrical pillar 38 in order to prevent separation of this valve element 23 by penetrating the inside face of valve element 23.

Furthermore, a pair of projections 39 of flange 28b whereon a holding member 30 is affixed are provided in the vicinity of cylindrical pillar 38.

Holding members 30 are formed of spring steel sheet or the like and comprise a central fixed part 30a and a resilient deforming part 30b linked thereto and bent in a curve from this central fixed part 30a in the radial direction and circumferential direction; holding members 30 are respectively fixed to the tip of shaft 28a of movable element 28 and to cylindrical pillar 38 of flange 28b.

In more detail, in the case of holding member 30 that is fixed to flange 28b, its central fixed part 30a is formed in annular shape such that cylindrical pillar 38 can be inserted thereinto and, at circumferentially spaced positions, is formed with a pair of cross-shaped engagement holes 40 into which can be pressed and fixed the pair of projections 39 that project from flange 28b of movable element 28; furthermore, its resilient deforming part 30b is formed with cross-shaped engaging holes 41 into which can be respectively pressed and fixed the pair of projections 34 provided on the end face of casing 21.

Also, as regards the holding member 30 that is fixed on shaft 28a, its central fixed part 30a is formed in practically a disc shape with a cross-shaped engagement hole 42 into which the tip of shaft 28a is pressed in and fixed being formed at its center; also, the outside end of resilient deforming part 30b thereof is connected to an annular connecting element 43 which is formed of the same external shape as the internal shape of recess 21b of casing 21.

Coil 29 is wound in a cylindrical shape such that it has a larger internal diameter than the external diameter of cylindrical part 26a of core 26 and has a smaller external diameter than the internal diameter of magnet 27; it is fixed by one end thereof being telescopically fitted on to a small-diameter part 28c formed at the end face of movable element 28 on the side where shaft 28a of flange 28b is provided, and is thereby integrated with this movable element 28.

Furthermore, the member indicated by reference symbol 44 in FIG. 3 is a stop-plate mounted on this casing 21 so as to cover the recess 21b formed in this casing 21 and is screwed in position by means of screws B.

Electrically-operated evacuation device 20 according to the present embodiment is assembled as follows.

First of all, core 2 is inserted from the side of flange 26a into accommodating hole 21a of casing 21 and yoke 25 which has a magnet 27 mounted on its inner circumference is inserted whilst pushing apart engagement claws 36 provided on casing 21. This core 26 and yoke 25 are thereby mounted in casing 21 by engagement of these engagement claws 36 with the end face of yoke 25.

Next, valve element 23 is mounted on cylindrical pillar 38 formed on flange 28b of movable element 28 and one of the holding members 30 is fixed by means of projections 39 to one face of flange 28b and furthermore coil 29 Is fixed by fitting telescopically on to a small-diameter part 28c on the other face of flange 28b; these movable element 28 and coil 29 are then Inserted into casing 21 and shaft 28a of movable element 28 is positioned within cylindrical part 26a of core 26 while coil 29 Is positioned in the gap between cylindrical part 26a of core 26 and yoke 25.

Then, one holding member 30 is pressed in and affixed in the end of casing 21 and the pair of projections 34 provided in its end face are pressed Into and fixed in engagement holes 41 formed in resilient deforming part 30b of holding member 30; also, the tip of shaft 28a of movable element 28 is made to project from the through-hole 31 formed in the bottom wall of casing 21 into recess 21b, the tip of this shaft 28a being thereby pressed into and fixed in engagement hole 42 formed in central fixing part 30a of the other holding member 30 that is inserted in recess 21b.

Also, if required, fixing at the locations where pressing-in of projections 34 and engagement holes 41 is effected and at the locations where pressing-in of shaft 28a and engagement hole 42 is effected may be reinforced by applying adhesive thereto.

By means of this operation, shaft 28a of movable element 28 is maintained in coaxial and non-contacting condition with respect to core 26 and coil 29 is maintained in non-contacting condition with respect to coil 26 and yoke 25.

After this, the electrically-operated evacuation device 20 of this embodiment is assembled by winding the ends of coil 29 on respective terminals 32 then fixing these two by means of solder or the like, fixing cover 33 to the end at the aperture side of casing 21 by means of screws B, and, in addition, fixing stop plate 44 by means of screws B so as to cover recess 21b of casing 21.

In this electrically-operated evacuation device 20 assembled as above, when drive current is applied to coil 29, movable element 28 and coil 29 are moved towards cover 33 in opposition to the resilient force of the two holding members 30, thereby causing valve element 23 that is mounted on movable element 28 to come into contact with evacuation port 22 formed in cover 33, blocking this evacuation port 22.

In this condition, supply of air into armband 1 becomes possible.

Also, in order to lower the pressure of armband 1 in order to measure the blood pressure, application of drive current to coil 29 is discontinued and movable element 28 and coil 29 are thereby shifted in the direction away from cover 33 by means of the restoring force of holding members 30 and the internal pressure of armband 1: as a result, valve element 23 is moved away from evacuation port 22, opening this evacuation port 22 and thereby evacuating the air within armband 1.

In this process, by controlling the pattern of application and stoppage of the drive current, the rate of evacuation can be maintained constant.

In such an opening/closure operation of evacuation port 22, since the moving parts constituted by movable element 28 and coil 29 are held in non-contacting condition with respect to yoke 25 and core 26, there is no frictional resistance, so smooth movement of movable element 28 is ensured and, as a result, drive control with no hysteresis and high response is made possible.

Also, since moving force of movable element 28 is applied by providing coil 29 integrally with movable element 28, movable element 28 can be formed by lightweight non-magnetic material such as plastics so, in addition to there being no frictional resistance, only a small attractive force becomes necessary for movement of movable element 28, making it possible to greatly reduce power consumption.

Also, since a magnetic path along the inside wall surface of casing 21 is formed by yoke 25 and core 26, leakage of magnetic flux is suppressed and for this reason also the force acts efficiently on coil 29, making it possible to reduce power consumption, as mentioned above.

Battery life can thereby be prolonged.

Also, to the extent that power consumption can be reduced, the number of turns of the coil can also be reduced, making it possible to employ a small overall external diameter, thereby enabling miniaturization to be achieved.

Furthermore, by forming fine irregularities 23b on the end face of valve element 23, the opening/closure operation of evacuation port 23 is performed gradually due to the resilient deformation of irregularities 23b in the initial period of opening/closing of evacuation port 22 by valve element 23, thereby making possible a pressure reduction operation with little fluctuation.

As described above, with an evacuation device for a sphygmomanometer according to this embodiment of the present invention, the moving parts of the means for driving that effect movement of the valve element are maintained in a non-contacting condition with respect to the other structural members; consequently, frictional resistance during opening/closure of the evacuation port is greatly reduced and loss of control precision caused by hysteresis can be prevented and the accuracy of the sphygmomanometry thereby raised.

Also, by reducing the drive force of the valve element, power consumption can be reduced and the life of the batteries can be extended.

Furthermore, to the extent that the attractive force to the movable element can be reduced, the number of turns of the coil can be reduced, thereby making it possible to reduce its external dimensions and achieve miniaturization.

Furthermore, by forming fine irregularities on the end face of the valve element, in the initial period of opening/closure of the evacuation port by the valve element, the opening/closure operation of the evacuation port is made gradual by this resilient deformation, thereby making it possible to achieve a pressure reduction operation with little fluctuation; as a result, pressure reduction at a highly constant rate can be achieved from the initial period of opening/closure. Thanks to the formation of these irregularities, extremely precise control of the pressure reduction characteristic in accordance with the desired curve can be achieved; previously this was extremely difficult. Specifically, in recent years, in order to achieve accurate sphygmomanometry, it is being demanded to effect pressure reduction not along a simple pressure reduction curve but rather along a specific pressure reduction curve prescribed by a computer; with the conventional evacuation device, control such as to effect pressure reduction along such a specific pressure reduction curve was extremely difficult. The present invention is epoch-making in that it solves this problem at a stroke. The precision of sphygmomanometry can thereby be enormously increased.

It should be noted that, although in the above embodiment valve element 10 was constituted of resilient material, it would, in contradistinction to this, be possible to adopt a construction in which resilient element 10 is constituted of stainless steel or the like while the portion of evacuation port 10a is constituted of a resilient member; or both valve element 10 and evacuation port 10a could be constituted by resilient members.

Also, although an example in which the minute irregularities are formed on valve element 10 has been described, it would, in contradistinction to this, be possible to provide these on locations of evacuation port 10a that contact valve element 10, or they could be provided on both valve elements 10 and evacuation port 10a.

Furthermore, although, in the embodiment described above, an example was described in which a sphygmomanometer was constructed using an electrically-operated evacuation device by applying a fluid flow rate regulation device according to the present invention, the fluid flow rate regulation device of the present invention is not restricted to this example of application and could be applied to all types of device in which fine flow rate regulation is necessary.

INDUSTRIAL APPLICABILITY

The present invention can be applied in fluid flow rate regulation devices capable of fine flow rate regulation and evacuation devices for sphygmomanometers whereby air that is supplied into an armband can be evacuated with constant velocity and to computer-controlled sphygmomanometers etc. which are of small power consumption, which can be miniaturized, and which can achieve high accuracy of measurement.

What is claimed is:

1. A fluid flow rate regulation device comprising a fluid passage port and a valve element that effects opening/closure of the fluid passage port, in which the flow rate of fluid flowing through said fluid passage port is regulated by regulating the degree of opening/closure of the valve element wherein:

fine irregularities are formed in said fluid passage port and/or valve element in at least a portion where the fluid passage port and valve element make contact, such that the opening/closure of the fluid passage port is performed gradually due to resilient deformation of the fine irregularities in an initial period of opening/closing of the fluid passage port by the valve element, thereby facilitating pressure reduction with the reduced fluctuation.

2. The fluid flow rate regulation device according to claim 1 wherein the portion in said fluid passage port and/or valve element where at least the fluid passage port and valve element make contact is constituted by a resilient member.

3. An evacuation device for a sphygmomanometer whereby air that is fed into an armband comprised by the sphygmomanometer is gradually evacuated, comprising:

an evacuation port whereby the air that is fed into said armband is evacuated, and a valve element that performs opening/closing of this evacuation port, wherein fine irregularities are formed on a portion in said evacuation port and/or valve element where at least the evacuation port and valve element make contact, such that the opening/closure of the evacuation port is performed due to resilient deformation of the fine irregularities in an initial period of opening/closing of the evacuation port by the valve element, thereby facilitating pressure reduction with reduced fluctuation.

4. The evacuation device for a sphygmomanometer according to claim 3 wherein the portion in said evacuation port and/or valve element where at least the evacuation port and valve element make contact is constituted by a resilient member.

5. A sphygmomanometer comprising:

an armband; a pump that supplies compressed air to the armband; a pressure meter that detects the air pressure within armband; an evacuation device that evacuates the air within said armband; and a microcomputer that supplies air at constant pressure to said armband by controlling the action of said pump in accordance with the detection signal from said pressure meter, and that evacuates air at a constant velocity from said armband by controlling the action of said evacuation device, wherein:

an evacuation device for a sphygmomanometer according to claim 3 employed as said evacuation device.

6. A sphygmomanometer comprising:

an armband; a pump that supplies compressed air to the armband; a pressure meter that detects the air pressure within said armband; an evacuation device that evacuates the air within said armband; and a microcomputer that supplies air at constant pressure to said armband by controlling the action of said pump in accordance with the detection signal from said pressure meter, and that evacuates air at a constant velocity from said armband by controlling the action of said evacuation device, wherein:

an evacuation device for a sphygmomanometer according to claim 3 is employed as said evacuation device.

7. A sphygmomanometer comprising:

an armband; a pump that supplies compressed air to the armband; a pressure meter that detects the air pressure within said armband; an evacuation device that evacuates the air within said armband; and a microcomputer that supplies air at constant pressure to said armband by controlling the action of said pump in accordance with the detection signal from said pressure meter, and that evacuates air at a constant velocity from said armband by controlling the action of said evacuation device, wherein:

an evacuation device for a sphygmomanometer according to claim 3 is employed as said evacuation device.

8. An evacuation device for a sphygmomanometer whereby air that is fed into an armband comprised by the sphygmomanometer is gradually evacuated, comprising:

a casing; a valve element that performs opening/closure of an aperture arranged in the casing; a cylindrical yoke provided with means for driving opening/closure of the valve element, the means for driving being mounted within said casing; a core provided with a cylindrical part arranged concentrically within the yoke and a flange abutted by one end of said yoke; a magnet that forms magnetic flux in the radial direction and that is arranged within said yoke with a separation with respect to said core; a movable element provided through the cylindrical part of said core, with said valve element integrally mounted at one end thereof; a coil arranged in the separation between said magnet and the core and fixed at one end of said movable element; and holding members interposed between both ends of said movable member and said casing and that holds said movable element and coil in non-contacting condition with respect to said core and yoke.

* * * * *